United States Patent [19]

Shiu

[11] 4,203,438
[45] May 20, 1980

[54] MOXA BURNER AND MOUNT FOR MULTIPLE MOXA BURNERS

[76] Inventor: Desmond K. Shiu, 660 Elm St., Montpelier, Vt. 05602

[21] Appl. No.: 10,346

[22] Filed: Feb. 8, 1979

[51] Int. Cl.² .............................................. A61F 7/00
[52] U.S. Cl. .................................................... 128/254
[58] Field of Search ............... 128/212, 254, 256, 399, 128/303.1, 362, 379, 402, 403

[56] References Cited

U.S. PATENT DOCUMENTS

| 540,566 | 6/1895 | Wilson | 128/254 |
|---|---|---|---|
| 1,817,823 | 8/1931 | Ito | 128/254 |
| 1,831,669 | 11/1931 | Kono | 128/254 |
| 2,602,449 | 7/1952 | Ruzsits | 128/256 |
| 3,946,733 | 3/1976 | Hon | 128/254 |

*Primary Examiner*—Lawrence W. Trapp

*Attorney, Agent, or Firm*—Sughrue, Rothwell, Mion, Zinn and Macpeak

[57] ABSTRACT

A moxa burner comprises inner and outer tubular housings. Helical grooves within one of the housings and vertical slots within the other housing carry projecting pins of a platform for varying the vertical position of the circular platform which is shifted axially by relative rotation of the two housings. A pair of relatively rotating rings which are perforated about their periphery at one end of the tubular housing control airflow entering the interior of the moxa burner. The fumes from burning of a moxa roll are directed axially to one open end of the burner for contact with the surface area of the human body at certain "associated effect points" for acupuncture treatment of human patients. Multiple moxa burners may be carried on a suitable mounting board and suspended by strings over the patient's shoulder for adjustable height location along the patient's acupuncture meridian lines.

4 Claims, 7 Drawing Figures

MOXA BURNER AND MOUNT FOR MULTIPLE MOXA BURNERS

BACKGROUND OF THE INVENTION

Acupuncture as a modern medical science phenomenon enjoys considerable favor recently in the western world, although the science of acupuncture is of ancient Chinese origin. In my U.S. Pat. No. 3,750,654, issued Aug. 7, 1973, and entitled "Physiotherapeutic Devices and Methods", it is brought out that in accordance with acupuncture teaching, the function of the internal organs of the body can be augmented by external stimulation of various anatomical parts in certain points, the so-called "associate effect points" located along the so-called bladder meridians. Stimulation of the spine provides beneficial effects on the kidneys and the like. Additional stimulation of other points on the same meridian provide beneficial effects on the working of other organs, including pericardium, heart, diaphragm, gall bladder, peritoneum, etc. Stimulation may be had on the soles of the feet, the muscles of the calves and various other parts of the human body.

In that patent, a roller of substantially circular cross section having a length substantially equal to the width of the back of an average human and having two rounded projections which are spaced apart by a distance such that when the roller is in contact with the back, the projections are located on opposite sides of the spine, is employed for highly beneficial stimulation of the acupuncture bladder meridians.

It has been further determined that a plant substance under the name Moxa and bearing the botanical name Artemesia Vulgaris, when burned, gives off a smoke which may be employed to fumigate and warm the skin's surface to produce therapeutic effects for the complete body and may be particularly employed to stimulate acupuncture points.

It is, therefore, a primary object of the present invention to provide an improved low cost moxa burner for burning a roll of moxa and for permitting the smoke and heat resulting from such burning to be employed in concentrated surface application to a limited portion of the human body, in particular in the vicinity of an acupuncture point.

It is a further object of this invention to provide a moxa burner applicator board supporting a plurality of moxa burners for contact with the human body and to permit the board suspended moxa burners suspended to contact the human body at vertically adjustable positions for application of moxa burner smoke along multiple acupuncture meridian lines to each side of the spine of an acupuncture patient.

SUMMARY OF THE INVENTION

The moxa burner for limited human surface area smoke application for acupuncture stimulation comprises a tubular outer housing having at least one spiral groove on its inner periphery, a tubular inner housing concentrically positioned within said outer housing and having a diameter slightly less than that of the outer tubular housing. The inner housing gears parallel, elongated, longitudinal slots at circumferentially spaced positions extending at least partially along the length of the inner housing. A circular platform having a diameter slightly less than that of the tubular inner housing is carried coaxially within the tubular inner housing and has pins projecting radially from the platform periphery at spaced circumferential positions corresponding to the tubular inner housing slots with the pins projecting through respective slots and having their ends received within the grooves of the tubular outer housing. An end of the tubular housing opens axially. Means are provided for mounting a roll of moxa to the platform and the moxa burner includes vent means for venting the interior of the tubular inner housing to the outside. Smoke resulting from burning of the moxa roll is caused to exit axially through the open end and impinge upon a portion of the human body in contact therewith for localized stimulation at a selected acupuncture point.

The tubular outer housing terminates at the end remote from the platform in a first annular ring bearing a plurality of circumferentially spaced holes. An outer ring of slightly larger diameter bearing similar circumferentially spaced holes is rotatably mounted concentrically about the inner ring and is rotated with respect thereto to permit the holes of the rings to be aligned or misaligned and to thereby control the flow of vent air to the interior of the moxa burner. The outer ring constitutes an inverted cup-shaped cover or cap bearing a central hole and a gauze disc is fitted between the cover and the inner ring at the end of the tubular outer housing for permitting the free flow of smoke resulting from the burning of the moxa roll to pass therethrough but preventing ashes resulting from the burning of the moxa roll from contacting the surface of the body which overlies the open end of the inverted cup-shaped cover. A U-shaped spring clip is preferably riveted to the platform at its center forming laterally spaced spring fingers within which is forcibly pressed one end of the moxa roll. The moxa roll is mounted coaxially within the tubular inner housing on the platform for movement towards and away from the gauze covered opening to control the application of moxa smoke and heat to the surface of the body overlying the cover opening.

A BRIEF DESCRIPTION OF THE DRAWINGS

DESCRIPTION OF THE PREFERRED EMBODIMENT

Figure 1:
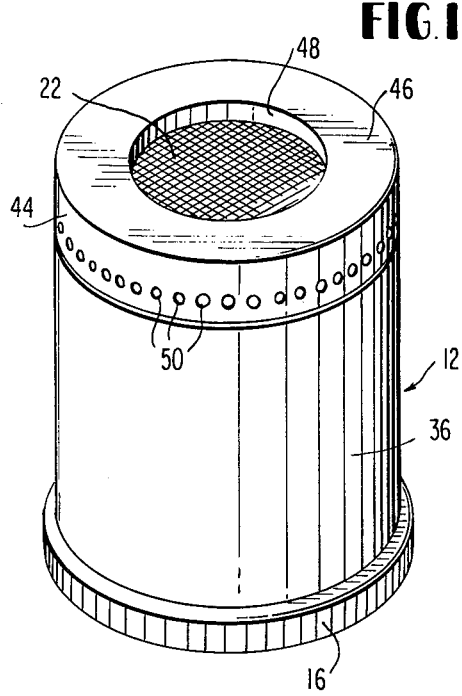
FIG. 1 is a perspective view of a moxa burner forming one embodiment of the present invention.
Figure 2:
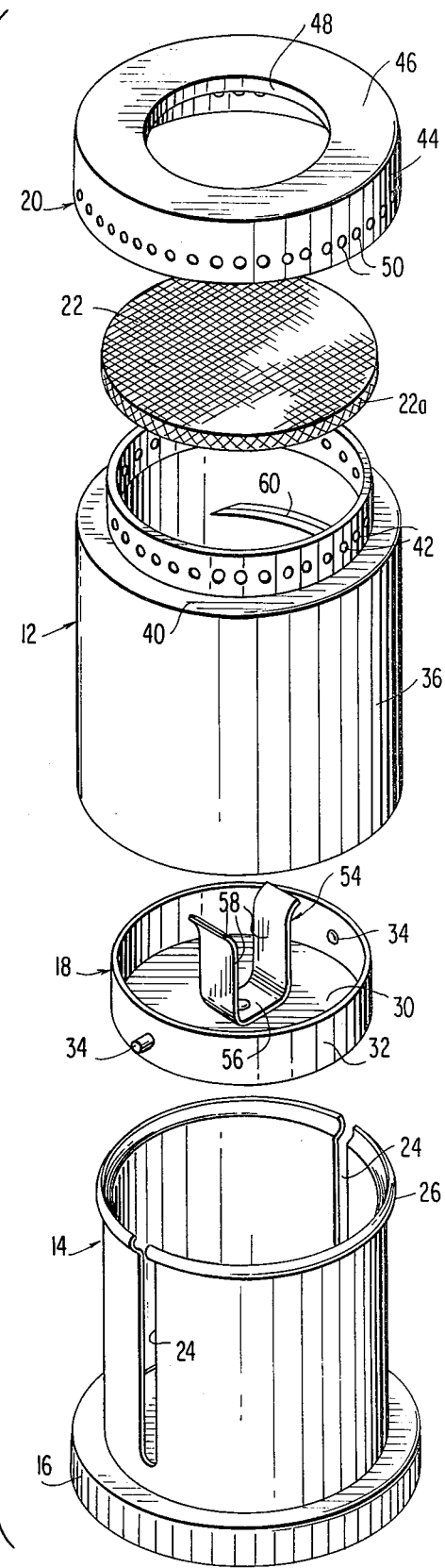
FIG. 2 is an exploded, perspective view of the components of the moxa burner of FIG. 1.
Figure 3:
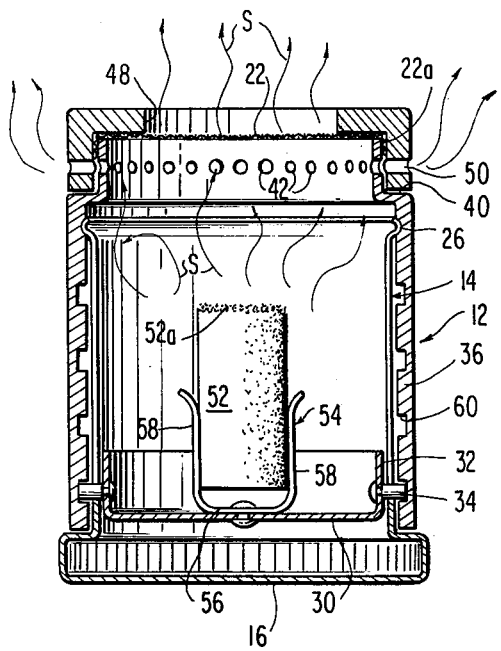
FIG. 3 is a vertical sectional view of the moxa burner of FIG. 1.

Referring to the drawings, FIGS. 1 through 5 inclusive, it is seen that the moxa burner indicated generally at 10 comprises as principal components a tubular outer housing indicated generally at 12; a tubular inner housing indicated generally at 14, terminating at its bottom in an integral capstan 16, a cup-shaped platform 18; an inverted apertured cup-shaped cover or cap indicated at 20; and a gauze disc 22. The tubular inner housing 14 is formed of sheet metal, has an integral radially enlarged projection portion or capstan 16 at the bottom and is provided with diametrically opposed, longitudinal slots 24 which extend upwardly from a point just above the capstan 16 to the upper end of the inner housing 14. Housing 14 terminates in an outwardly rounded lip 26 and, while being closed at the bottom by way of capstan bottom wall 28, is open at its upper end. The platform 18, as indicated previously, is cup-shaped, includes a bottom wall 30 and an annular sidewall 32, and is of a diameter slightly less than the diameter of the tubular inner housing 14. The annular sidewall 32 bears diametrically opposed pins 34 which project radially outwardly from the periphery of the annular sidewall 32 and are of a diameter slightly less than the width of the slots 24 of housing 14 within which they ride. The platform is caused to move axially and to therefore rise vertically within the diametrically opposed slots 34 of the inner housing 14. The tubular outer housing indicated at 12 comprises a hollow, cylindrical wall 36 and which may be formed of a thermal insulation material, terminating at its upper end in a reduced diameter portion or inner ring 38 forming an annular ledge 40. The ring 38 bears a plurality of small diameter circumferentially spaced, perforations or holes 42. The inverted, cup-shaped gauze disc 22 has a diameter slightly larger than the diameter of the inner ring 38 and is positioned on that ring so as to overlie the open upper end of the tubular outer housing 12. Further, the inverted cup-shaped cover or cap 20 which may also be formed of a thermal insulation material is comprised of an annular sidewall or outer ring 44 and a top wall 46 which is apertured centrally at 48 providing a relatively large opening permitting the axial passage of moxa smoke for direct contact with a limited area of the human body, that is, the portion overlying the opening 48 within cover 20. The annular sidewall or outer ring 44 is apertured as at 50 with small diameter holes equal in size and at circumferentially spaced positions corresponding to those at 42 within the inner ring 38. The annular wall 44 or outer ring forms with ring 38 a two-part air valve for controlling the ventilation of air entry into the interior of the tubular inner housing 14 which bears the moxa roll for burning.

In that respect, the moxa roll 52 which is cylindrical in form, is mounted vertically on the platform 18 by the use of a U-shaped spring clip indicated generally at 54 and being formed of a central base 56 and a pair of opposed, integral outwardly flared spring fingers 58. The fingers 58 may be spread apart to permit one end of the moxa roll 52 to be frictionally force fitted to the spring clip 54 as per FIG. 3. The upper end of the moxa roll 52 is ignited as at 52a and burns, giving off the smokes which escape from the upper end of the moxa burner. Most of the smokes pass through the gauze disc 22.

The gauze disc 22 is shown as having an annular lip as at 22a, although the gauze disc could be a pure flat disc form and simply be in edge contact with the upper end of the ring 38. In order to vary the rate of burning of the moxa roll and the application of the smoke and heat to the surface of the patient overlying the cover opening 48 and in contact with that cover, the outer ring 44 is rotated relative to the outer tubular housing 12 inner ring 38 to align or offset the holes of respective rings, thus varying the ventilation or intake of air to the area of combustion as at 52a of moxa roll 52.

Figure 4:
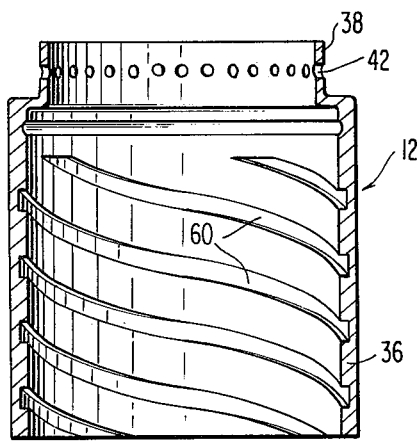
FIG. 4 is a vertical sectional view of the tubular outer housing.
Figure 5:
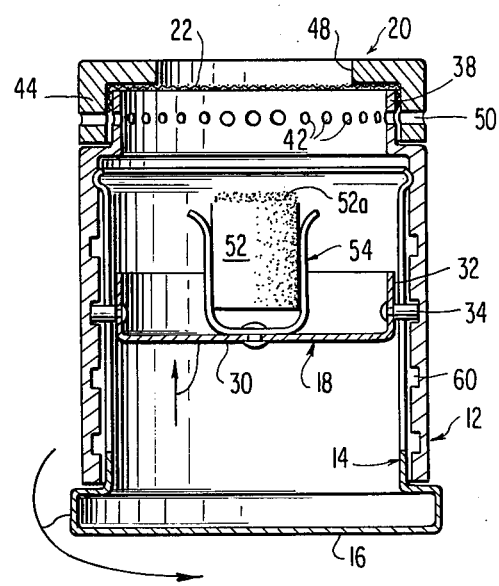
FIG. 5 is a vertical sectional view similar to that of FIG. 3 with the platform shifted axially to a raised position by rotation of the capstan.

The platform 18 may be raised and lowered by a rotation of capstan 28 of the inner housing 14 relative to the outer housing 12. In order to accomplish this, particularly as shown in FIGS. 4 and 5, the tubular outer housing 12 bears a plurality of helical grooves as at 60 on its inner periphery, within the main body portion beneath the inner ring 38. The helical grooves receive the projecting ends of pins 34 which also pass through the diametrically opposed slots 24 of the tubular inner housing 14. Thus, as the capstan 28 is rotated, the pins 34 bearing the platform are caused to ride vertically upward as the pins are driven along a helical path defined by the grooves 60. Grooves 60 are of rectangular cross section and are given a certain pitch. As may be seen, the pins ride in different helical grooves within the inner periphery of that member. The desired shift in position as the moxa roll burns down may be seen by comparison of FIG. 3, at an early stage of burning, against the later stage, FIG. 5, where the moxa roll has been substantially reduced to half its length by the combustion process.

Figure 6:
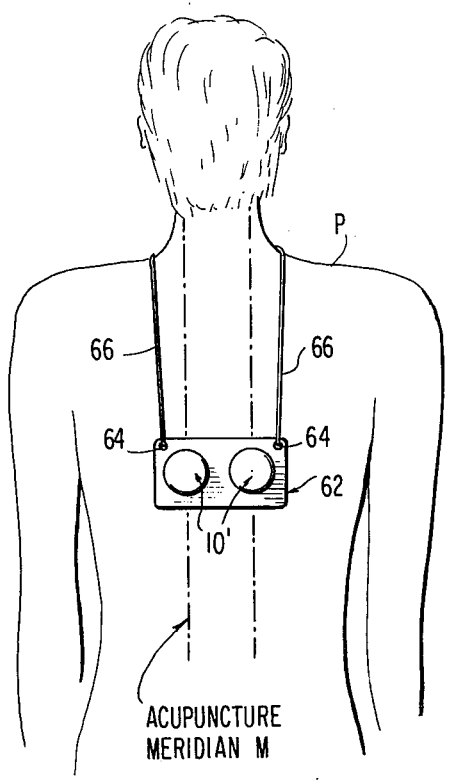
FIG. 6 is a rear view of an acupuncture patient bearing a multiple moxa burner unit treatment board forming a second aspect of the present invention.

The moxa burner 10 may be used individually on any given acupuncture point of the human body. Further, a pair of such burners 10, FIG. 6, may be carried on a treatment platform or mounting board as at 62 so that plural points one on each side of the body, may be stimulated. As indicated, the mounting board 62 is of a rectangular configuration and is provided with holes passing through the same at the upper corners as at 64. Strings or cords 66 project respectfully from the holes 64 with the cords being tied (not shown) at the front of the human patient P, whereby the vertical height of the board 62 may be varied depending upon the acupuncture point locations requiring treatment along the vertical acupuncture meridian as at M, FIG. 6.

Figure 7:
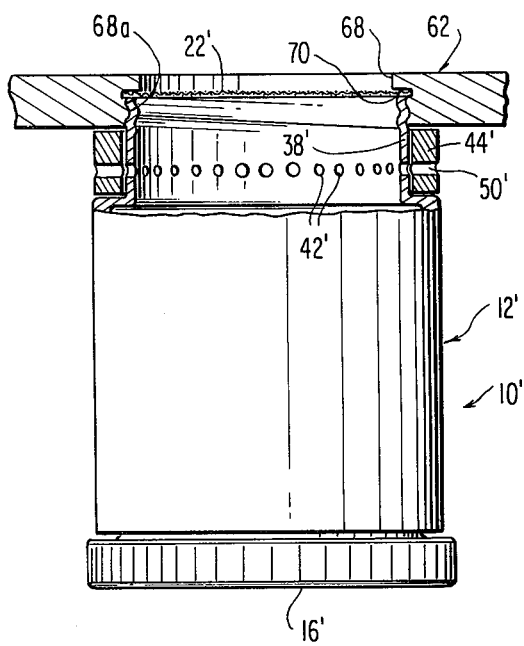
FIG. 7 is a top plan view of a portion of the assembly of FIG. 6, partially broken away to show the mounting of one of the moxa burners to the treatment mounting board.

By reference to FIG. 7, it may be seen that the board 62 is provided with two relatively large diameter holes as at 68 corresponding generally to the size of the inner ring 38' of the tubular outer housing 12' of the individual moxa burners 10' in this embodiment of the invention. In this case, the outer ring 44' does not constitute a cover or cup but simply an open ended annular ring having a series of circumferentially spaced small diameter perforations 50 similar to the perforations or holes 50 within the cover 20 of the embodiment of FIGS. 1 through 5 inclusive. Further, the inner ring 38' integral with and constituting a smaller diameter, radially offset portion of the tubular outer housing 12' terminates at its upper end in a threaded portion 38'a which is threaded to an enlarged diameter threaded portion 68a of opening 68 against a shoulder 70. The upper end of the inner ring 38' presses the circular gauze disc 22' against shoulder 70 in this embodiment. The inner ring 38' is provided with circumferentially spaced small diameter holes 42', of a number corresponding to the holes 50' in the outer ring 44' such that by rotation of the ring 44' relative to ring 48', the extent of ventilation of the interior of the moxa burner is readily changed to vary the combustion rate of the moxa roll (not shown). In this embodiment, capstan 28 is rotated relative to the outer tubular housing 12' to effect a vertical shift in the platform and the moxa roll (not shown) carried thereby, the embodiment of FIG. 7 being identical in most respects to FIGS. 1 through 5 inclusive. For replacement of the moxa roll, it is necessary only to unthread the ring 38; at the threaded portion 38'a, leaving the end of the gauze 22' separated from the ring 38'. Access may be readily had to the clip carried by the platform in this embodiment to supply a new moxa roll for further smoke and heat treatment of the surface areas of the body which overlies the openings 68 within the mounting board 62 bearing, respectively, burners 10'. As mentioned, the strings or cords 66 permit the mounting board and the pair of moxa burners to be lowered on the patient's back, from the front of the body for purposes of self therapy.

While the invention has been particularly shown and described with reference to a preferred embodiment thereof, it will be understood by those skilled in the art that various changes in form and details may be made therein without departing from the spirit and scope of the invention.

What is claimed is:

1. A moxa burner for applying the smoke and heat generated by burning of a moxa roll to a limited surface area of the human body about an acupuncture point or the like, said moxa burner comprising:
    a tubular outer housing bearing spiral grooves on the inner wall thereof,
    a tubular inner housing having a diameter slightly less than the diameter of said tubular outer housing and concentrically mounted therein,
    a plurality of parallel, longitudinal slots within said tubular inner housing, at circumferentially spaced positions,
    a circular platform having a diameter less than that of said tubular inner housing, being mounted coaxially therewithin and bearing pins projecting radially from the platform periphery at circumferentially spaced positions corresponding to said tubular inner housing slots, being received by said slots and projecting within said spiral grooves of said tubular outer housing; whereby, rotation of said tubular inner housing with respect to said tubular outer housing causes said platform to move longitudinally,
    a closure overlying one end of said tubular outer housing and being apertured centrally to permit the moxa smoke and heat to be discharged axially from said moxa burner for contact with the human body,
    vent means for venting the interior of said tubular inner housing to the atmosphere for controlling burning of the moxa roll, and
    means for mounting said moxa roll on said platform facing said cover and movable with said platform towards and away from said opening within said cover.

2. The moxa burner as claimed in claim 1, wherein said outer housing at the end bearing said cover comprises an inner ring, said cover is rotatably mounted on said one end of said tubular outer housing and constitutes an outer ring, said rings bearing circumferentially spaced small diameter holes at corresponding axial planes, such that rotation of said cover relative to said tubular outer housing causes said holes to shift from aligned to offset position to vary the ventilation of the air interiorly to said tubular inner housing.

3. The moxa burner as claimed in claim 2, further comprising a gauze screen overlying the end of said tubular outer housing and being sandwiched between said tubular outer housing and said cover, to prevent ash contact resulting from burning of the moxa roll to contact the surface of the body overlying the open end of said cover.

4. A multiple unit moxa burner assembly for treatment of multiple acupuncture points simultaneously along an acupuncture meridian line of a human patient or the like, said unit comprising:
    a rectangular mounting board, said board having laterally opposed holes at respective corners along one side of said board,
    strings fixed at one end to the holes at the corners of said board and being tie-able at the front of the patient after passing over the shoulders or opposite sides of the patient's body for variably adjusting the vertical height of said mounting board,
    a pair of laterally spaced holes within said board,
    a pair of moxa burners mounted to said board at said holes, each moxa burner comprising a tubular outer housing having spiral grooves on the inner wall thereof and being threaded at one end to said mounting board at said holes and in axial alignment therewith,
    a gauze disc overlying the threaded open end of said tubular outer housing and being pressed against said mounting board at said hole,
    a plurality of circumferentially spaced small diameter holes within said tubular outer housing adjacent said threaded end,
    an outer ring rotatably mounted on said tubular outer housing overlying said circumferentially spaced small diameter holes and bearing corresponding small diameter holes in a circumferential array such that by rotation of said outer ring, the holes of the outer ring may be aligned or misaligned with the holes within said tubular outer housing so as to vary the ventilation of the interior of said tubular outer housing,
    a tubular inner housing having a diameter slightly less than that of said tubular outer housing and being concentrically carried internally of said tubular outer housing, said tubular inner housing bearing parallel, longitudinally extending, circumferentially spaced slots,
    a circular platform having a diameter slightly less than the diameter of said tubular inner housing and being mounted coaxially within said tubular inner housing and bearing radially projecting pins on the periphery of the same with said pins extending through said circumferentially spaced, longitudinal slots within said tubular inner housing and being received within the spiral grooves on the inner wall of said tubular outer housing such that by rotation of said tubular inner housing relative to said tubular outer housing, said platform shifts axially,
    means for fixedly mounting a moxa roll to said platform facing said gauze disc; whereby, said platform can be shifted axially to compensate for burning of the moxa roll to control the flow of smoke and heat generated during burning of the moxa roll through said mounting board holes for contact with the portions of the human body overlying the holes for respective moxa burners.

* * * * *